United States Patent [19]

Harada et al.

[11] Patent Number: 5,648,510
[45] Date of Patent: Jul. 15, 1997

[54] PROCESS FOR PREPARATION OF DIARYL CARBONATE

[75] Inventors: Katsumasa Harada; Yoichi Imbe; Keigo Nishihira; Shuji Tanaka; Satoru Fujitsu; Ryoji Sugise; Koichi Kashiwagi; Toshihiko Sumida, all of Yamaguchi, Japan

[73] Assignee: Ube Industries, Ltd., Yamaguchi, Japan

[21] Appl. No.: 627,897

[22] Filed: Apr. 3, 1996

[30] Foreign Application Priority Data

Apr. 4, 1995 [JP] Japan .................................... 7-078766

[51] Int. Cl.⁶ .................................................. C07C 69/96
[52] U.S. Cl. ................................................... 558/274
[58] Field of Search ..................... 558/274, 272

[56] References Cited

U.S. PATENT DOCUMENTS

| | | |
|---|---|---|
| 4,182,726 | 1/1980 | Illuminati . |
| 4,544,507 | 10/1985 | Foley . |
| 5,136,077 | 8/1992 | Rand ........................................ 558/274 |

*Primary Examiner*—Gary Geist
*Assistant Examiner*—Jean F. Vollano
*Attorney, Agent, or Firm*—McAulay Fisher Nissen Goldberg & Kiel, LLP

[57] ABSTRACT

A diaryl carbonate is prepared at a high yield and a high selectivity by heating a diaryl oxalate in the presence of an organic phosphorous compound to release carbon monoxide therefrom. A halogen atom-containing compound can be employed in combination with the organic phosphorous compound.

16 Claims, No Drawings

PROCESS FOR PREPARATION OF DIARYL CARBONATE

FIELD OF THE INVENTION

The present invention relates to a process for preparing a diaryl carbonate which does not employ phosgene as its starting compound. In more detail, the invention relates to a process for preparing a diaryl carbonate from a diaryl oxalate.

BACKGROUND OF THE INVENTION

The diaryl carbonate is utilized in industry to prepare a polycarbonate resin. Heretofore, the diaryl carbonate is prepared by causing a reaction between phosgene and an aromatic hydroxyl compound in the presence of an alkali (see Japanese Patent Provisional Publication No. 62(1987)-190146). This process has disadvantages in that the toxic phosgene is necessarily employed and a great amount of an alkali is used.

Another process for the preparation of a diaryl carbonate is known which comprises transesterification between a dialkyl carbonate and an aromatic hydroxy compound in the presence of a catalyst (see Japanese Patent Publications No. 56(1981)-42577 and H1(1989)-5588). This transesterification process, however, also has a disadvantage in that its reaction rate is not high even if a highly active catalyst is employed. This means that a large scaled apparatus is required when a diaryl carbonate is produced in an industrially applicable scale.

Yuki Gosei Kagaku (Organic Synthetic Chemistry in Japan), 5, Report 47, pp. 70–71(1948) teaches a reaction in which diphenyl oxalate is heated to release carbon monoxide to give diphenyl carbonate. This report does not mention with respect to the yield and selectivity of the reaction. According to a trace experiment of the experiment set forth in this report, only a small amount of diphenyl carbonate is produced.

U.S. Pat. No. 4,544,507 describes a process for the production of a carbonate diester which involves heating an oxalate diester in a liquid medium containing an alcoholate catalyst to yield carbonate diester and carbon monoxide.

SUMMARY OF THE INVENTION

It is a principal object of the present invention to provide a new process for preparing a diaryl carbonate which does not use phosgene and which gives enough selectivity and yield.

It is another object of the invention to provide a process for preparing a diaryl carbonate which is advantageously employable for industrial use.

It is a further object of the invention to provide a process for preparing a diaryl carbonate which shows a high selectivity and a high yield and therefore is advantageously employable in industrial production of a diaryl carbonate.

The present invention resides in a process for preparing a diaryl carbonate which comprises heating a diaryl oxalate in the presence of an organic phosphorous compound to release carbon monoxide therefrom.

The invention also resides in a process for preparing a diaryl carbonate which comprises heating a diaryl oxalate in the presence of an organic phosphorous compound and a halogen atom-containing compound to release carbon monoxide therefrom.

In the above-mentioned processes, the organic phosphorous compound preferably has a trivalent or pentavalent phosphorous atom, and advantageously has at least one carbon-phosphorus bonding. Preferred organic phosphorous compounds are a phosphonium salt, a phosphine, a phosphine dihalide, and a phosphine oxide, such as a tetraarylphosphonium salt, a triarylphosphine, a triarylphosphine dihalide, and a triarylphosphine oxide.

In the latter process, the halogen atom-containing compound can be an organic or inorganic halide compound.

DETAILED DESCRIPTION OF THE INVENTION

The process for preparing a diaryl carbonate from a diaryl oxalate can be illustrated as follows:

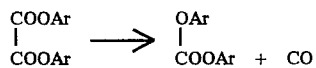

wherein Ar stands for an unsubstituted or substituted. aryl group.

The aryl group of diaryl oxalate can be a phenyl or naphthyl group which can be substituted with an alkyl group of 1–12 carbon atoms (e.g., methyl or ethyl), an alkoxy group of 1–12 carbon atoms (e.g., methoxy or ethoxy), a halogen atom (e.g., fluorine or chlorine), or other substituent groups such as nitro. One or more substituent groups can be attached to any position of the aryl group. Accordingly, any isomers can be included. Examples of the substituted aryl groups include o-(or m- or p-)methylphenyl, o-(or m- or p-)ethylphenyl, o-(or m- or p-)methoxyphenyl, o-(or m- or p-)ethoxyphenyl, o-(or m- or p-)fluorophenyl, o-(or m- or p-)chlorophenyl, and o-(or m- or p-)nitrophenyl.

In the preparation processes of the present invention, the organic phosphorous compound preferably has a trivalent or pentavalent phosphorous atom, and advantageously has at least one carbon-phosphorus bonding. Preferred are organic phosphorous compounds having three or more carbon-phosphorus bondings. Preferred organic phosphorous compounds are a phosphonium salt having the following formula (A), a phosphine having the following formula (B), a phosphine dihalide having the following formula (C), and a phosphine oxide having the following formula (D):

Formula (A):

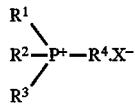

Formula (B):

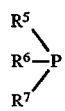

Formula (C):

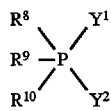

Formula (D):

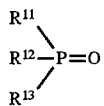

In the above-described formulas, each of $R^1$, $R^2$, $R^3$, $R^4$, $R^5$, $R^6$, $R^7$, $R^8$, $R^9$, $R^{10}$, $R^{11}$, $R^{12}$, and $R^{13}$ represents an aryl group of 6 to 10 carbon atoms, an alkyl group of 1 to 16 carbon atoms, an aralkyl group of 7 to 22 carbon atoms, an aryloxy group of 6 to 10 carbon atoms, or a heterocyclic group of 4 to 16 carbon atoms, X represents a counter ion of the phosphonium ion, and each of $Y^1$ and $Y^2$ represents a halogen atom.

Detailed descriptions are given below for the phosphonium salt of formula (A), the phosphine of formula (B), the phosphine dihalide of formula (C), and the phosphine oxide of formula (D).

(A) Phosphonium Salt

Formula (A):

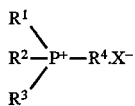

The phosphonium salt can be represented by the above formula (A), wherein each of $R^1$, $R^2$, $R^3$ and $R^4$, independently represents an aryl group of 6 to 10 carbon atoms, an alkyl group of 1 to 16 carbon atoms, an aralkyl group of 7 to 22 carbon atoms, an aryloxy group of 6 to 10 carbon atoms, or a heterocyclic group of 4 to 16 carbon atoms, and X represents a counter ion of the phosphonium ion. Any two of $R^1$, $R^2$, $R^3$ and $R^4$ may be combined to form a ring having the phosphorus atom as its ring member.

The aryl group is described in more detail. The aryl group can be a phenyl or naphthyl group. The phenyl or naphthyl group can have one or more substituents in any positions. Examples of the substituents include alkyl of 1 to 16 carbon atoms, preferably of 1 to 12 carbon atoms (e.g., methyl, ethyl, n-propyl, isopropyl, n-butyl, isobutyl, sec-butyl, or tert-butyl), alkoxy of 1 to 15 carbon atoms, preferably of 1 to 12 carbon atoms (e.g., methoxy, ethoxy, n-propoxy, isopropoxy, n-butoxy, isobutoxy, sec-butoxy, or tert-butoxy), alkoxycarbonyl of 2 to 12 carbon atoms, preferably of 2 to 8 carbon atoms (e.g., methoxycarbonyl or ethoxycarbonyl), aryl (e.g., phenyl), amino such as N,N-disubstituted amino (e.g., N,N-dimethylamino), cyano, nitro, and halo (e.g., fluoro, chloro, or bromo).

The alkyl group is described in more detail. The alkyl group can have 1 to 16 carbon atoms. Examples of the alkyl group include methyl, ethyl, n-propyl, isopropyl, n-butyl, isobutyl, sec-butyl, or tert-butyl. The alkyl group can have one or more substituents in any positions. Examples of the substituents are the same as those described for the substituents of the aryl group.

The aralkyl group is described in more detail. The aralkyl group can have 7 to 22 carbon atoms. Examples of the aralkyl group include benzyl, phenethyl and naphthylmethyl. The aralkyl group can have one or more substituents in any positions. Examples of the substituents are the same as those described for the substituents of the aryl group.

The aryloxy group is described in more detail. The aryloxy group can be a phenoxy or naphthoxy group. The aryloxy group can have one or more substituents in any positions. Examples of the substituents are the same as those described for the substituents of the aryl group.

The heterocyclic group is described in more detail. The heterocyclic group can have 4 to 16 carbon atoms. Examples of the heterocyclic group include thienyl, furyl, and pyridyl. The heterocyclic group can have one or more substituents in any positions. Examples of the substituents are the same as those described for the substituents of the aryl group.

The groups of $R^1$, $R^2$, $R^3$ and $R^4$ of the phosphonium salt can be the same or different from each other. For instance, all of the groups of $R^1$, $R^2$, $R^3$ and $R^4$ are aryl groups in one phosphonium salt, that is, a tetraarylphosphonium salt. Three of the groups are aryl groups and other one is another group, that is, a triarylphosphonium salt. Two of the groups are aryl groups and other two are other groups, that is, a diarylphosphonium salt. Only one of the groups is an aryl group and other three are other groups, that is, an arylphosphonium salt. All of the groups of $R^1$, $R^2$, $R^3$ and $R^4$ are other than the aryl groups. Preferred are the tetraarylphosphonium salt and an arylphosphonium salt in which three of the groups of $R^1$, $R^2$, $R^3$ and $R^4$ are aryl groups and other one is a heterocyclic group.

The counter ion ($X^-$) can be a halide ion (e.g., chloride ion, bromide ion, or iodide ion), a hydrogen dihalide ion (e.g., hydrogen dichloride ion, hydrogen dibromide ion, hydrogen diiodide ion, or hydrogen bromide chloride ion), a halogen acid ion (e.g., chlorate ion, bromate ion, or iodate ion), a per-halogen acid ion (e.g., perchlorate ion, perbromate ion, or periodate ion), an aliphatic carboxylate ion (e.g., acetate ion, trifluoroacetate ion, or propionate ion), an aromatic carboxylate ion (e.g., benzoate ion, or α- or β-naphthalenecarboxylate ion), an aromatic hydroxy ion (e.g., phenoxide ion), an inorganic acid ion (e.g., sulfate ion, sulfite ion, phosphate ion, phosphite ion, borate ion, hydrogenborate ion, cyanate ion, thiocyanate ion, or fluoroborate ion), an alkylsulfonate or alkylsulfinate ion having an alkyl group of 1 to 16 carbon atoms (e.g., methyl, ethyl, n-propyl, or isopropyl), an arylsulfonate or arylsulfinate ion having an aryl group (e.g., phenyl, p-tolyl, or p-nitorophenyl), a tetraalkylborate ion having an alkyl group of 1 to 10 carbon atoms (e.g., tetramethylborate ion, or tetraethylborate ion), or a tetraarylborate ion (e.g., tetraphenylborate ion, or tetrakis-p-fluorophenylborate ion). Examples of preferred counter ions ($X^-$) include halide ions such as chloride ion, bromide ion and iodide ion, and hydrogen dihalide ions such as hydrogen dichloride ion, hydrogen dibromide ion, hydrogen diiodide ion, and hydrogen bromide chloride ion. Most preferred are chloride ion and hydrogen dichloride ion.

Concrete examples of the preferred phosphonium salts of the formula (A) are described below.

(1) Phosphonium salt in which all of $R^1$, $R^2$, $R^3$ and $R^4$ are aryl groups and $X^-$ is a halide ion Examples are tetraphenylphosphonium chloride, tetraphenylphosphonium bromide, tetraphenylphosphonium iodide, tetrakis(p-chlorophenyl)phosphonium chloride, tetrakis(p-fluorophenyl)phosphonium chloride, tetrakis(p-tolyl) phosphonium chloride, p-chlorophenyltriphenylphosphonium chloride, p-chlorophenyltriphenylphosphonium bromide, p-chlorophenyltriphenylphosphonium iodide, p-tolyltriphenylphosphonium chloride, p-tolyltriphenylphosphonium bromide, p-tolyltriphenylphosphonium iodide, m-trifluoromethylphenyltriphenylphosphonium chloride, p-biphenyltriphenylphosphonium chloride, m-methoxyphenyltriphenylphosphonium chloride, p-methoxyphenyltriphenylphosphonium chloride, p-ethoxyphenyltriphenylphosphonium chloride, p-ethoxyphenyltriphenylphosphonium bromide,
p-ethoxyphenyltriphenylphosphonium iodide,
p-dimethylaminophenyltriphenylphosphonium chloride,
p-ethoxycarbonylphenyltriphenylphosphonium chloride,
m-cyanophenyltriphenylphosphonium chloride, and 1-naphthyltriphenylphosphonium chloride. Most preferred is tetraphenylphosphonium chloride.

(2) Phosphonium salt in which all of $R^1$, $R^2$, $R^3$ and $R^4$ are aryl groups and $X^-$ is a hydrogen dihalide ion Examples are tetraphenylphosphonium hydrogen dichloride, tetraphenylphosphonium hydrogen dibromide, tetraphenylphosphonium hydrogen diiodide, and tetraphenylphosphonium hydrogen bromide chloride. Most preferred is tetraphenylphosphonium hydrogen dichloride.

(3) Phosphonium salt in which all of $R^1$, $R^2$, $R^3$ and $R^4$ are aryl groups and $X^-$ is an aliphatic carboxylate ion Examples are tetraphenylphosphonium acetate, p-chlorophenyltriphenylphosphonium acetate, p-ethoxyphenyltriphenylphosphonium acetate, p-tolyltriphenylphosphonium acetate, and tetraphenylphosphonium trifluoroacetate.

(4) Phosphonium salt in which all of $R^1$, $R^2$, $R^3$ and $R^4$ are aryl groups and $X^-$ is fluoroborate ion Examples are tetraphenylphosphonium fluoroborate, p-chlorophenyltriphenylphosphonium fluoroborate, p-ethoxyphenyltriphenylphosphonium fluoroborate, and p-tolyltriphenylphosphonium fluoroborate.

(5) Phosphonium salt in which all of $R^1$, $R^2$, $R^3$ and $R^4$ are aryl groups and $X^-$ is thiocyanide ion An example is tetraphenylphosphonium thiocyanide.

(6) Phosphonium salt in which three of $R^1$, $R^2$, $R^3$ and $R^4$ are aryl groups, one is an alkyl group, and $X^-$ is a halide ion Examples are methyltriphenylphosphonium chloride, methyltriphenylphosphonium bromide, methyltriphenylphosphonium iodide, ethyltriphenylphosphonium chloride, ethyltriphenylphosphonium bromide, ethyltriphenylphosphonium iodide, n-propyltriphenylphosphonium chloride, n-propyltriphenylphosphonium bromide, n-propyltriphenylphosphonium iodide, isopropyltriphenylphosphonium chloride, isopropyltriphenylphosphonium bromide, n-dodecyltriphenylphosphonium chloride, n-dodecyltriphenylphosphonium bromide, chloromethyltriphenylphosphonium chloride, methyltris(m-chlorophenyl)phosphonium chloride, methyltris(m-chlorophenyl)phosphonium bromide, ethyltris(m-chlorophenyl)phosphonium chloride, and ethyltris(m-chlorophenyl)phosphonium bromide.

(7) Phosphonium salt in which three of $R^1$, $R^2$, $R^3$ and $R^4$ are aryl groups, one is an aralkyl group, and $X^-$ is a halide ion Examples are benzyltriphenylphosphonium chloride, p-fluorobenzyltriphenylphosphonium chloride, p-fluorobenzyltriphenylphosphonium bromide, 2,4-dichlorobenzyltriphenylphosphonium chloride, 2,4-dichlorobenzyltriphenylphosphonium bromide, p-n-butoxybenzyltriphenylphosphonium chloride, p-n-butoxybenzyltriphenylphosphonium bromide, 2-naphthylmethyltriphenylphosphonium chloride, 2-naphthylmethyltriphenylphosphonium bromide, 9-fluorenyltriphenylphosphonium chloride, and 9-fluorenyltriphenylphosphonium bromide.

(8) Phosphonium salt in which three of $R^1$, $R^2$, $R^3$ and $R^4$ are aryl groups, one is a heterocyclic group, and $X^-$ is a halide ion An example is 2-thiophenetriphenylphosphonium chloride.

(9) Phosphonium salt in which three of $R^1$, $R^2$, $R^3$ and $R^4$ are aryl groups, one is an aryloxy group, and $X^-$ is a halide ion An example is phenoxytriphenylphosphonium chloride.

(10) Phosphonium salt in which three of $R^1$, $R^2$, $R^3$ and $R^4$ are aryl groups, one is an alkyl group, and $X^-$ is an aliphatic carboxylate ion Examples are methyltriphenylphosphonium acetate, ethyltriphenylphosphonium acetate, and n-propyltriphenylphosphonium acetate.

(11) Phosphonium salt in which three of $R^1$, $R^2$, $R^3$ and $R^4$ are aryl groups, one is an alkyl group, and $X^-$ is a fluoroborate ion Examples are methyltriphenylphosphonium fluoroborate, ethyltriphenylphosphonium fluoroborate, and n-propyltriphenylphosphonium fluoroborate.

(12) Phosphonium salt in which two of $R^1$, $R^2$, $R^3$ and $R^4$ are aryl groups, other two are other groups, and $X^-$ is a halide ion Examples are dimethyldiphenylphosphonium chloride, diethyldiphenylphosphonium chloride, dimethyldiphenylphosphonium bromide, and diethyldiphenylphosphonium bromide.

(13) Phosphonium salt in which one of $R^1$, $R^2$, $R^3$ and $R^4$ are aryl groups, other three are other groups, and $X^-$ is a halide ion Examples are diethylmethylphenylphosphonium chloride, and diethylmethylphenylphosphonium bromide.

(14) Phosphonium salt in which none of $R^1$, $R^2$, $R^3$ and $R^4$ are aryl groups, and $X^-$ is a halide ion Examples are tetra-n-butylphosphonium chloride, and tetra-n-butylphosphonium bromide.

Some of the above-mentioned phosphonium salts are known and available on market. Other phosphonium salts can be prepared by the processes set forth in Bull. Chem. Soc. Jpn., 56, 2869 (1983) and J. Am. Chem. Soc., 70, 737 (1948), or processes similar to those described in these publications.

For instance, the tetraarylphosphonium chloride can be prepared by reacting a triarylphosphine and an aryl halide (e.g., aryl iodide or aryl bromide) in the presence of a palladium acetate catalyst and treating the resulting tetraarylphosphonium iodide or bromide with an ion exchange resin (chloride type) to give the desired tetraarylphosphonium chloride. The produced tetraarylphosphonium chloride is preferably dried. For the drying, the tetraarylphosphonium chloride is preferably heated to 100° to 200° C. for 0.5 to 5 hours in a stream of a dry inert gas such as dry argon gas and then heated to 80° to 200° C. for 0.5 to 2 hours in a stream of a dry hydrogen chloride gas. The commercially available tetraarylphosphonium chloride is also preferred to be subjected to the above-mentioned process.

The tetraarylphosphonium salt having a counter ion other than halide ion can be prepared by reacting the above-obtained tetraarylphosphonium chloride with an alkali metal salt (e.g., sodium salt or potassium salt) or an ammonium salt of the desired counter ion, that is, ion exchange reaction. Other phosphonium salts other than the tetraaryl phosphonium salts can be prepared in the same manner or an analogous manner. These phosphonium salts are also preferred to be subjected to the drying treatment, in advance of its use as the catalyst.

(B) Phosphine

Formula (B):

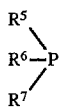

The phosphine can be represented by the above formula (B), wherein each of $R^5$, $R^6$ and $R^7$ independently represents an aryl group, an alkyl group of 1 to 16 carbon atoms, an aralkyl group of 7 to 22 carbon atoms, or a heterocyclic group of 4 to 16 carbon atoms. Any two of $R^5$, $R^6$ and $R^7$ may be combined to form a ring having the phosphorus atom as its ring member.

Examples of the aryl group, alkyl group, aralkyl group and heterocyclic group are the same as those described for the phosphonium salt of the formula (A).

The groups of $R^5$, $R^6$ and $R^7$ of the phosphine can be the same or different from each other. For instance, all of the groups of $R^5$, $R^6$ and $R^7$ are aryl groups in one phosphine, that is, a triarylphosphine. Two of the groups are aryl groups and other one is another group, that is, a diarylphosphine. Only one of the groups is an aryl group and other two are other groups, that is, an arylphosphine. All of the groups of $R^5$, $R^6$ and $R^7$ are other than the aryl groups. Preferred is the phosphine in which all of the groups of $R^5$, $R^6$ and $R^7$ are aryl groups.

Concrete examples of the preferred phosphines of the formula (B) are described below.

(1) Phosphine in which all of $R^5$, $R^6$ and $R^7$ are aryl groups (i.e., triarylphosphine)

Examples are triphenylphosphine, tris(p-chlorophenyl) phosphine, tris (p-tolyl) phosphine, and α-naphthyl (phenyl) -p-methoxyphenylphosphine.

(2) Phosphine in which two of $R^5$, $R^6$ and $R^7$ are aryl groups and one is other group (i.e., diarylphosphine)

Examples are methyldiphenylphosphine and phenyl (p-methoxyphenyl) methylphosphine.

(3) Phosphine in which one of $R^5$, $R^6$ and $R^7$ is an aryl group and other two are other groups (i.e., arylphosphine)

Examples are dimethyl (phenyl)phosphine and ethyl (phenyl)n-propylphosphine.

(4) Phosphine in which none of $R^5$, $R^6$ and $R^7$ are aryl groups

Examples are benzyl (n-butyl)methylphosphine and tributylphosphine. An example of a phosphine in which any two of $R^5$, $R^6$ and $R^7$ are combined to form a ring having the phosphorus atom as its ring member is phenylbiphenylenephosphine.

(C) Phosphine Dihalide

Formula (C):

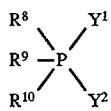

The phosphine dihalide can be represented by the above formula (C), wherein each of $R^8$, $R^9$ and $R^{10}$ independently represents an aryl group, an alkyl group of 1 to carbon atoms, an aralkyl group of 7 to 22 carbon atoms, or a heterocyclic group of 4 to 16 carbon atoms, and each of $Y^1$ and $Y^2$ independently represents a halogen atom such as chlorine, bromine or iodine. Any two of $R^8$, $R^9$ and $R^{10}$ may be combined to form a ring having the phosphorus atom as its ring member.

Examples of the aryl group, alkyl group, aralkyl group and heterocyclic group are the same as those described for the phosphonium salt of the formula (A).

The groups of $R^8$, $R^9$ and $R^{10}$ of the phosphine dihalide can be the same or different from each other. For instance, all of the groups of $R^8$, $R^9$ and $R^{10}$ are aryl groups in one phosphine, that is, a triarylphosphine dihalide. Two of the groups are aryl groups and other one is another group, that is, a diarylphosphine dihalide. Only one of the groups is an aryl group and other two are other groups, that is, an arylphosphine dihalide. All of the groups of $R^8$, $R^9$ and $R^{10}$ are other than the aryl groups. Preferred is the phosphine dihalide in which all of the groups of $R^8$, $R^9$ and $R^{10}$ are aryl groups.

Concrete examples of the preferred phosphine dihalides of the formula (C) are triphenylphosphine dichloride, triphenylphosphine dibromide, and triphenylphosphine diiodide.

(D) Phosphine Oxide

Formula (D):

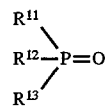

The phosphine oxide can be represented by the above formula (D), wherein each of $R^{11}$, $R^{12}$ and $R^{13}$ independently represents an aryl group, an alkyl group of 1 to 16 carbon atoms, an aralkyl group of 7 to 22 carbon atoms, or a heterocyclic group of 4 to 16 carbon atoms. Any two of $R^{11}$, $R^{12}$ and $R^{13}$ may be combined to form a ring having the phosphorus atom as its ring member.

Examples of the aryl group, alkyl group, aralkyl group and heterocyclic group are the same as those described for the phosphonium salt of the formula (A).

The groups of $R^{11}$, $R^{12}$ and $R^{13}$ of the phosphine oxide can be the same or different from each other. For instance, all of the groups of $R^{11}$, $R^{12}$ and $R^{13}$ are aryl groups in one phosphine, that is, a triarylphosphine oxide. Two of the groups are aryl groups and other one is another group, that is, a diarylphosphine oxide. Only one of the groups is an aryl group and other two are other groups, that is, an arylphosphine oxide. All of the groups of $R^{11}$, $R^{12}$ and $R^{13}$ are other than the aryl groups. Preferred is the phosphine oxide in which all of the groups of $R^{11}$, $R^{12}$ and $R^{13}$ are aryl groups.

Concrete examples of the preferred phosphine oxides of the formula (D) are described below.

(1) Phosphine oxide in which all of $R^{11}$, $R^{12}$ and $R^{13}$ are aryl groups (i.e., triarylphosphine oxide)

Examples are triphenylphosphine oxide, tris (p-chlorophenyl)phosphine oxide, tris (p-tolyl)phosphine oxide, and α-naphthyl(phenyl)-p-methoxyphenylphosphine oxide.

(2) Phosphine oxide in which two of $R^{11}$, $R^{12}$ and $R^{13}$ are aryl groups and one is other group (i.e., diarylphosphine oxide)

Examples are methyldiphenylphosphine oxide and phenyl (p-methoxyphenyl)methylphosphine oxide.

(3) Phosphine oxide in which one of $R^{11}$, $R^{12}$ and $R^{13}$ is an aryl group and other two are other groups (i.e., aryl phosphine oxide)

Examples are dimethyl(phenyl)phosphine oxide and ethyl (phenyl)n-propylphosphine oxide.

(4) Phosphine oxide in which none of $R^{11}$, $R^{12}$ and $R^{13}$ are aryl groups Examples are benzyl (n-butyl) methylphosphine oxide and tributylphosphine oxide. An example of a phosphine in which any two of $R^{11}$, $R^{12}$ and $R^{13}$ are combined to form a ring having the phosphorus atom as its ring member is phenylbiphenylenephosphine oxide.

Among the above-mentioned organic phosphorous compounds, tetraarylphosphoniumhalide, tetraarylphosphonium hydrogen dihalide, and triarylphosphine dihalide are preferred. Most preferred are tetraarylphosphonium chloride, tetraarylphosphonium hydrogen dichloride, and triarylphosphine dichloride. The organic phosphorous compound can be employed singly or in combination in the process of the present invention. The organic phosphorous compound can be dissolved or dispersed in the reaction medium.

The organic phosphorous compound can be employed in an amount of 0.001 to 50 mol. %, preferably 0.01 to 20 mol. %, based on the amount of diaryl oxalate (100 mol. %).

In the reaction for releasing or eliminating carbon monoxide (CO) according to the invention, a halogen atom-containing compound can be incorporated. Particularly, in the cases where a phosphonium salt other than phosphonium halide and phosphonium hydrogen dihalide are used as the phosphorous compound and where a phosphonium halide or a phosphonium hydrogen dihalide is used in a small amount, the incorporation of a halogen atom-containing compound is preferred. The halogen atom-containing compound preferably is a chlorine atom-containing compound or a bromine atom-containing compound. Most preferred is a chlorine atom-containing compound. The incorporated halogen atom-containing compound can be decomposed or changed into other halogen atom-containing compound in the course of the development of the reaction.

The halogen atom-containing compound is generally employed in an amount of 0.001 to 300 moles, preferably 0.1 to 100 moles per one mole of the organic phosphorous compound.

The halogen atom-containing compound may be an inorganic compound or an organic compound.

Examples of the inorganic halogen atom-containing compounds are halides of aluminum (e.g., aluminum chloride and aluminum bromide), halides of metals belonging to the platinum group (e.g., platinum chloride, ruthenium chloride, palladium chloride, and chloroplatinic acid), halides of phosphorus (e.g., phosphorus trichloride, phosphorus pentachloride, phosphorus oxychloride, phosphorus tribromide, phosphorus pentabromide, and phosphorus oxybromide), hydrogen halides (e.g., hydrogen chloride and hydrogen bromide), halides of sulfur (e.g., thionyl chloride, sulfuryl chloride, sulfur dichloride, and disulfur dichloride), and halogens per se (e.g., chlorine and bromine).

The organic halogen atom-containing compound preferably contains (1) carbon atom, (2) a halogen atom such as chlorine atom or a bromine atom, and (3) at least one of other atoms selected from a hydrogen atom, a nitrogen atom, a sulfur atom, and a silicon atom.

Examples of the organic halogen atom-containing compounds are organic compounds having a C-Hal bonding (in which Hal means a halogen atom), a C-Si-Hal bonding, a —C(O)-Hal bonding or a C—S(O)$_2$-Hal bonding. The organic halogen atom-containing compound can contain one or more halogen atoms such as chlorine(s), bromine(s) or iodine(s) singly or in combination.

Examples of the organic compound having a C-Hal bonding include alkyl halides (e.g., chloroform, carbon tetrachloride, 1,2-dichloroethane, butyl chloride, and dodecyl chloride), aralkyl halides (e.g., benzyl chloride, benzotrichloride, triphenylmethyl chloride, and α-bromo-o-xylene), and halogenated aliphatic nitriles (e.g., β-chloropropionitrile, and γ-chlorobutyronitrile), halogenated aliphatic carboxylic acids (e.g., chloroacetic acid, bromoacetic acid, and chloropropionic acid).

Examples of the organic compound having a C-Si-Hal bonding include halogenated silanes (e.g., diphenyldichlorosilane, and triphenylchlorosilane).

Examples of the organic compound having a —C(O)-Hal bonding include acylhalides (e.g., acetyl chloride, oxalyl chloride, propionyl chloride, stearoyl chloride, benzoyl chloride, 2-naphthalenecarboxylic acid chloride, and 2-thiophenecarboxylic acid chloride), halogenated formic acid aryl esters (e.g., phenyl chloroformate), and halogenated glyoxylic acid aryl esters (e.g., phenyl chloroglyoxylate).

Examples of the organic compound having a C—S(O)$_2$-Hal bonding include sulfonyl chlorides (e.g., p-toluenesulfonic acid chloride, and 2-naphthalenesulfonic acid chloride).

The reaction for releasing CO from a diaryl oxalate according to the invention can be conducted at a temperature in the range of 100° to 450° C., preferably 160° to 450° C., more preferably 180° to 400° C., most preferably 180° to 350° C., in an appropriate reaction vessel in the presence of the organic phosphorous compound, and optionally a halogen atom-containing compound. The reaction can be performed in a liquid phase in a batch system or a continuous system. In the course of progress of the reaction, carbon monoxide is emitted and the desired diaryl carbonate is formed. The reaction is generally conducted under an atmospheric pressure or under a reduced pressure. If the reaction temperature is higher than the reflux temperature of the starting diaryl oxalate, the reaction is preferably performed under pressure. There are no specific limitations with respect to the material of the reaction vessel. Ordinary reaction vessels such as of glass or stainless (SUS) can be employed.

The reaction does not require any solvent. However, if necessary, an organic solvent which does not pertain in the reaction can be employed. Such solvents can be diphenyl ether, sulforane, N-methylpyrrolidone, dimethylimidazolidone, or 1,3-dimethyl-3,4,5,6-tetrahydro-2(1H)-pyrimidinone.

After the reaction is complete, the resulting diaryl carbonate can be recovered and purified by distillation.

The present invention is further described by the following non-limitative examples. In the examples, the "conversion ratio of diaryl oxalate" (i.e., ratio of amount of consumed (or reacted) diaryl oxalate per the amount of charged diaryl oxalate), "selectivity to diaryl carbonate" (i.e., ratio of the amount of produced diaryl carbonate per the amount of consumed diaryl oxalate), and "yield" (i.e., ratio of the amount of produced diaryl carbonate per the amount of charged diaryl oxalate) are all expressed in terms of molar percent ratio (i.e., mol. %).

Reference Example 1

Synthesis of p-chlorophenyltriphenylphosphonium iodide [Reference: Bull. Chem. Soc. Jpn., 56, 2869 (1983)]

In 100 mL-volume egg-plant type flask, 3.30 g (11.4 mmol) of triphenylphosphine and 3.00 g (12.6 mmol) of p-chloroiodobenzene were dissolved in 40 mL of xylene. To the solution was added 30.0 mg (0.134 mmol) of palladium acetate, and the resulting mixture was stirred at 150° C. for 9.5 hours. After the reaction was complete, the reaction mixture was cooled to room temperature, and the precipitate was collected on a filter by suction. The collected precipitate was washed with xylene and dried under reduced pressure at 130° C. for 3 hours. There was obtained 5.48 g (yield: 87%)

of p-chlorophenyltriphenylphosphonium iodide (m.p.: 219°–222° C., elemental analysis: found: C 57.84%, H 3.74%, calculated: C 57.57%, H 3.82%).

Reference Example 2

Synthesis of p-chlorophenyltriphenylphosphonium chloride [Reference: J. Am. Chem. Soc., 70, 737 (1948)]

In 50 mL-volume egg-plant type flask, 1.00 g (2.00 mmol) of p-chlorophenyltriphenylphosphonium iodide and 10 mL (14 mg equivalent) of Amberlite IRA-400 (highly basic ion exchange resin, chloro-type, available from Organo Co., Ltd.) were stirred in an ion-exchanged water at room temperature for 1 hour. Subsequently, the ion exchange resin was filtered off, and the resin was washed with a small amount of an ion-exchanged water. The washing and the filtrate were combined to obtain 25 mL of an aqueous solution. To the solution was added 6.50 g of sodium chloride. The precipitate produced was collected on a filter by suction and dissolved in 30 mL of methylene chloride. Insolubles were filtered off, and the filtrate was added to 30 mL of ether. The precipitate produced was washed with ether and successively dried in the stream of dry argon gas at 120° C. for 1 hour, at 150° C. for 1 hour, and 180° C. for 1 hour. The dried product was then placed in contact with a stream of dry hydrogen chloride at 180° C. for 30 minutes. Thus treated product was further heated to 180° C. in a stream of dry argon gas for 1 hour, and then cooled to room temperature. There was obtained 0.63 g (yield: 77%) of p-chlorophenyltriphenylphosphonium chloride (m.p.: 158°–160° C.).

Reference Example 3

Synthesis of tetraphenylphosphonium thiocyanide

In 50 mL-volume egg-plant type flask, 1 g of tetraphenylphosphonium chloride was dissolved in 10 mL of water. To the solution was added 10 mL of an aqueous solution containing a theoretical amount of ammonium thiocyanate. The resulting mixture was stirred at room temperature for 0.5 hour. The precipitate produced was collected by filtration and washed with water three times. The precipitate was then re-precipitated from a mixture of methylene chloride and ether (1/2, vol/vol). The precipitate was washed with methylene chloride and dried at 160°–200° C. in a stream of argon under reduced pressure. There was obtained 0.88 g (yield: 83%) of tetraphenylphosphonium thiocyanide (m.p.: over 300° C.).

Other Reference Examples

Various phosphonium chlorides were prepared from the corresponding iodides or bromides in the similar manner as those described in Reference Examples 1 and 2. The products were heated and treated with hydrogen chloride in the similar manner as those in Reference Example 2 before they were employed as catalyst. Tetraphenylphosphonium trifluoroacetate was prepared in the similar manner as that in Reference Example 3.

The yields and other data of the produced phosphonium salts are set forth in Table 1.

TABLE 1

| Phosphonium Salt | X | Yield (%) | M.P. (°C.) | Analysis (Found) C | H | N |
|---|---|---|---|---|---|---|
| (p-F-Ph)$_4$P.X | I | 75 | >300 | 53.33 | 2.85 | — |
| | Cl | 97 | >300 | | | |
| (p-Cl-Ph)$_4$P.X | I | 56 | >300 | 47.79 | 2.47 | — |
| | Cl | 96 | >300 | | | |
| (p-Me-Ph)$_4$P.X | I | 58 | 275–278 | 64.20 | 5.11 | — |
| | Cl | 93 | >300 | | | |
| (p-Cl-Ph)PPh$_3$.X | I | 87 | 219–222 | 57.84 | 3.74 | — |
| | Cl | 77 | 158–160 | | | |
| (p-Me-Ph)PPh$_3$.X | I | 85 | 214–217 | 62.43 | 4.61 | — |
| | Cl | 98 | 177–180 | | | |
| (p-Ph-Ph)PPh$_3$.X | Br | 42 | 210–214 | 72.62 | 4.86 | — |
| | Cl | 86 | 225–229 | | | |
| (p-MeO-Ph)PPh$_3$.X | I | 87 | 223–226 | 60.20 | 4.37 | — |
| | Cl | 78 | 215–218 | | | |
| (p-Me$_2$N-Ph)PPh$_3$.X | Br | 84 | 278–282 | 67.52 | 5.57 | 3.04 |
| | Cl | 76 | 270–273 | | | |
| (p-EtO$_2$C-Ph)PPh$_3$.X | I | 59 | 215–218 | 60.41 | 4.44 | — |
| | Cl | 69 | 91–95 | | | |
| (m-CF$_3$-Ph)PPh$_3$.X | I | 32 | 194–197 | 56.50 | 3.53 | — |
| | Cl | 68 | 145–149 | | | |
| (m-MeO-Ph)PPh$_3$.X | I | 84 | 204–207 | 60.51 | 4.47 | — |
| | Cl | 79 | 260–267 | | | |
| (m-NC-Ph)PPh$_3$.X | Br | 9 | 222–225 | 67.82 | 4.38 | 2.91 |
| | Cl | 99 | 100–105 | | | |
| (1-naphthyl)PPh$_3$.X | I | 25 | 282–285 | 65.14 | 4.13 | — |
| | Cl | 84 | 271–274 | | | |
| (2-thiophene)PPh$_3$.X | I | 32 | 288–290 | 56.22 | 3.79 | — |
| | Cl | 99 | 162–165 | | | |
| Ph$_4$P.X | SCN | 83 | >300 | 75.46 | 5.06 | 3.67 |
| Ph$_4$P.X | CF$_3$CO$_2$ | 69 | 227 | 69.00 | 4.39 | — |

Example 1

In a 50 mL-volume glass flask equipped with a thermometer, a stirrer and a reflux condenser, a mixture of 6.0 g (24.8 mmol) of diphenyl oxalate and 0.093 g (0.25 mmol) of tetraphenylphosphonium chloride (PPh$_4$.Cl) was heated to 255° C. under an atmospheric pressure. At that temperature, the mixture was subjected to decarbonylation reaction (reaction for releasing CO) for 3 hours with removal of the produced carbon monoxide. The tetraphenylphosphonium chloride was heated and treated with hydrogen chloride in the same manner as those described in Reference Example 2, before it was employed as the catalyst.

After the reaction was complete, the reaction mixture was cooled to room temperature and analyzed by gas chromatography. It was confirmed that the conversion ratio of diphenyl oxalate was 96.2%, and 5.05 g (23.6 mmol) of diphenyl carbonate was produced; selectivity 99.0%; yield 95.2%.

Examples 2 to 4

The decarbonylation reaction was repeated in the manner as described in Example 1, except that the amount of tetraphenylphosphonium chloride, the amount of diphenyl oxalate, the reaction temperature and the reaction time were changed as set forth in Table 2.

The results are also set forth in Table 2.

Examples 5 to 9

The decarbonylation reaction was repeated in the manner as described in Example 1, except that tetraphenylphosphonium chloride was replaced with that set forth in Table 2, and that the amount of diphenyl oxatate, the reaction temperature and the reaction time were changed as set forth in Table 2. The tetraphenylphosphonium bromide employed was of the commercially available grade. The tetraphenylphosphonium hydrogen dichloride was prepared by the known process (Z. anorg. allg. chem., 551, 179 (1987).

The results are also set forth in Table 2.

TABLE 2

| Example No. | Catalyst (mol. % to DPO) | DPO (mmol) | Tem. (°C.) | Time (hr.) | DPO Con. (%) | DPC Sel. (%) | DPC Yield (%) |
|---|---|---|---|---|---|---|---|
| Ex. 1 | Ph$_4$P.Cl (1) | 24.8 | 255 | 3 | 96.2 | 99.0 | 95.2 |
| Ex. 2 | Ph$_4$P.Cl (5) | 20.7 | 220 | 3 | 99.0 | 99.0 | 98.0 |
| Ex. 3 | Ph$_4$P.Cl (10) | 20.7 | 200 | 3 | 97.8 | 96.6 | 94.5 |
| Ex. 4 | Ph$_4$P.Cl (0.2) | 20.7 | 280 | 1 | 98.0 | 99.0 | 97.0 |
| Ex. 5 | Ph$_4$P.Br (4.3) | 19.6 | 260 | 1 | 69.0 | 82.0 | 56.6 |
| Ex. 6 | Ph$_4$P.HCl$_2$ (0.5) | 20.7 | 260 | 3 | 99.0 | 99.0 | 98.0 |
| Ex. 7 | (p-F-Ph)$_4$P.Cl (0.5) | 20.7 | 260 | 3 | 99.0 | 99.0 | 98.0 |
| Ex. 8 | (p-Cl-Ph)$_4$P.Cl (0.5) | 20.7 | 260 | 3 | 99.0 | 99.0 | 98.0 |
| Ex. 9 | (p-Me-Ph)$_4$P.Cl (0.5) | 20.7 | 260 | 3 | 65.0 | 90.0 | 58.5 |

Remarks: The amount of the catalyst (organic phosphorous compound) is set forth in terms of mol. % based on the amount of DPO (diphenyl oxalate).
DPC: diphenyl carbonate
Ph$_4$P.Cl: tetraphenylphosphonium chloride
Ph$_4$P.Br: tetraphenylphosphonium bromide
Ph$_4$P.HCl$_2$: tetraphenylphosphonium hydrogen dichloride
(p-F-Ph)$_4$P.Cl: tetrakis(p-fluorophenyl)phosphonium chloride
(p-Cl-Ph)$_4$P.Cl: tetrakis(p-chlorophenyl)phosphonium chloride
(p-Me-Ph)$_4$P.Cl: tetrakis(p-tolyl)phosphonium chloride Comparison Example 1

The decarbonylation reaction was repeated in the manner as described in Example 1, except that 3.97 g (16.4 mmol) of diphenyl oxalate was employed and no tetraphenylphosphonium chloride was employed.

It was confirmed that the conversion ratio of diphenyl oxalate (DPO) was 0%, and that no diphenyl carbonate (DPC) was produced.

Comparison Example 2

The decarbonylation reaction was repeated in the manner as described in Example 1, except that 5.0 g (20.7 mmol) of diphenyl oxalate was employed, the reaction temperature was changed to 330° C., and no tetraphenylphosphonium chloride was employed.

It was confirmed that the conversion ratio of diphenyl oxalate was 10.8%, and that 0.18 g (0.84 mmol) of diphenyl carbonate was produced; selectivity 37.7%; yield 4.1%.

Comparison Example 3

In a closable 90 mL-volume stainless-made reaction vessel equipped with a thermometer and a stirrer, a mixture of 5.0 g (20.7 mmol) of diphenyl oxalate, 0.5 g (3.8 mmol) of potassium phenolate, and 5.0 g of tetrahydrofuran was heated to 100° C. At that temperature, the mixture was subjected to decarbonylation reaction for 3 hours.

It was confirmed that the conversion ratio of diphenyl oxalate was 0%, and that no diphenyl carbonate was produced.

The reaction conditions and results of Comparison Examples 1 to 3 are set forth in Table 3.

TABLE 3

| Com. Ex. No. | Catalyst (mol. % to DPO) | DPO (mmol) | Tem. (°C.) | Time (hr.) | DPO Con. (%) | DPC Sel. (%) | DPC Yield (%) |
|---|---|---|---|---|---|---|---|
| Com. Ex. 1 | — | 16.4 | 255 | 3 | 0 | 0 | 0 |
| Com. Ex. 2 | — | 20.7 | 330 | 3 | 10.8 | 37.7 | 4.1 |
| Com. Ex. 3 | PhOK (18) | 20.7 | 100 | 3 | 0 | 0 | 0 |

Remarks: The amount of the catalyst (potassium phenolate) is set forth in terms of mol. % based on the amount of DPO (diphenyl oxalate).
PhOK: potassium phenolate Examples 10 to 18

The decarbonylation reaction was repeated in the manner as described in Example 1, except that tetraphenylphosphonium chloride was replaced with the phosphonium salt set forth in Table 4, and that the amount of diphenyl oxalate and the reaction temperature were changed as set forth in Table 4.

The results are also set forth in Table 4.

TABLE 4

| Example No. | Catalyst (0.5 mol. %) to DPO) | DPO (mmol) | Tem. (°C.) | Time (hr.) | DPO Con. (%) | DPC Sel. (%) | DPC Yield (%) |
|---|---|---|---|---|---|---|---|
| Ex. 10 | (p-Cl-Ph)PPh$_3$.Cl | 20.7 | 260 | 3 | 99.0 | 98.0 | 97.0 |
| Ex. 11 | (p-Me-Ph)PPh$_3$.Cl | 20.7 | 260 | 3 | 97.0 | 98.0 | 95.1 |
| Ex. 12 | (p-Ph-Ph)PPh$_3$.Cl | 20.7 | 260 | 3 | 99.0 | 98.0 | 97.0 |
| Ex. 13 | (p-MeO-Ph)PPh$_3$.Cl | 20.7 | 260 | 3 | 67.0 | 61.0 | 40.9 |
| Ex. 14 | (p-Me$_2$N-Ph)PPh$_3$.Cl | 20.7 | 260 | 3 | 99.0 | 99.0 | 98.0 |
| Ex. 15 | (p-EtO$_2$C-Ph)PPh$_3$.Cl | 20.7 | 260 | 3 | 85.0 | 99.0 | 84.2 |
| Ex. 16 | (m-CF$_3$-Ph)PPh$_3$.Cl | 20.7 | 260 | 3 | 96.0 | 99.0 | 95.0 |
| Ex. 17 | (m-MeO-Ph)PPh$_3$.Cl | 20.7 | 260 | 3 | 97.0 | 97.0 | 94.1 |
| Ex. 18 | (m-NC-Ph)PPh$_3$.Cl | 20.7 | 260 | 3 | 96.0 | 98.0 | 94.1 |

Remarks:
(p-Cl-Ph)PPh$_3$.Cl: p-chlorophenyltriphenylphosphonium chloride
(p-Me-Ph)PPh$_3$.Cl: p-tolyltriphenylphosphonium chloride
(p-Ph-Ph)PPh$_3$.Cl: p-biphenyltriphenylphosphonium chloride
(p-MeO-Ph)PPh$_3$.Cl: p-methoxyphenyltriphenylphosphonium chloride
(p-Me$_2$N-Ph)PPh$_3$.Cl: p-dimethylaminotriphenylphosphonium chloride
(p-EtO$_2$C-Ph)PPh$_3$.Cl: p-ethoxycarbonyl-phenyltriphenyl phosphonium chloride
(m-CF$_3$-Ph)PPh$_3$.Cl: m-trifluoromethylphenyltriphenyl-phosphonium chloride
(m-MeO-Ph)PPh$_3$.Cl: m-methoxyphenyltriphenylphosphonium chloride
(m-NC-Ph)PPh$_3$.Cl: m-cyanophenyltriphenylphosphonium chloride

Examples 19 to 23

The decarbonylation reaction was repeated in the manner as described in Example 1, except that tetraphenylphosphonium chloride was replaced with the phosphonium salt set forth in Table 5, and that the amount of diphenyl oxalate and the reaction temperature were changed as set forth in Table 5.

The results are also set forth in Table 5.

TABLE 5

| Example No. | Catalyst (mol. % to DPO) | DPO (mmol) | Tem. (°C.) | Time (hr.) | DPO Con. (%) | DPC Sel. (%) | DPC Yield (%) |
|---|---|---|---|---|---|---|---|
| Ex. 19 | (1-na)PPh$_3$.Cl (0.5) | 20.7 | 260 | 3 | 99.0 | 99.0 | 98.0 |
| Ex. 20 | (2-th)PPh$_3$.Cl (0.5) | 20.7 | 260 | 3 | 99.0 | 99.0 | 98.0 |
| Ex. 21 | MePPh$_3$.Br (5) | 20.7 | 255 | 3 | 45.1 | 64.5 | 29.1 |
| Ex. 22 | ClCH$_2$—PPh$_3$.Cl (0.5) | 20.7 | 260 | 3 | 35.0 | 96.0 | 33.6 |
| Ex. 23 | PhCH$_2$—PPh$_3$.Cl (0.5) | 20.7 | 260 | 3 | 47.0 | 89.0 | 41.8 |
| Ex. 24 | (p-Cl-Ph)$_3$P (5) | 24.8 | 255 | 3 | 99.4 | 81.6 | 81.1 |
| Ex. 25 | Ph$_3$PCl$_2$ (5) | 24.8 | 255 | 3 | 98.7 | 93.0 | 91.8 |
| Ex. 26 | Ph$_3$P=O (5) | 24.8 | 255 | 3 | 11.6 | 94.0 | 10.9 |

Remarks:
(1-na)PPh$_3$.Cl: 1-naphthyltriphenylphosphonium chloride
(2-th)PPh$_3$.Cl: 2-thiophenetriphenylphosphonium chloride
MePPh$_3$.Br: methyltriphenylphosphonium bromide
ClCH$_2$—PPh$_3$.Cl: chloromethyltriphenylphosphonium chloride
PhCH$_2$—PPh$_3$.Cl: benzyltriphenylphosphonium chloride
(p-Cl-Ph)$_3$P: tris(p-chlorophenyl)phosphine
Ph$_3$PCl$_2$: triphenylphosphine dichloride
Ph$_3$P=O: triphenylphosphine oxide

Example 24

The decarbonylation reaction was repeated in the manner as described in Example 1, except that tetraphenylphosphonium chloride was replaced with 1.24 mmol of tris(p-chlorophenyl)phosphine.

It was confirmed that the conversion ratio of diphenyl oxalate was 99.4%, the selectivity was 81.6%, and the yield was 81.1%.

Example 25

The decarbonylation reaction was repeated in the manner as described in Example 1, except that tetraphenylphosphonium chloride was replaced with 1.24 mmol of triphenylphosphine dichloride.

It was confirmed that the conversion ratio of diphenyl oxalate was 98.7%, the selectivity was 93.0%, and the yield was 91.8%.

Example 26

The decarbonylation reaction was repeated in the manner as described in Example 1, except that tetraphenylphosphonium chloride was replaced with 1.24 mmol of triphenylphosphine oxide. The charged diphenyl oxalate contained 3,000 ppm of chloride ion.

It was confirmed that the conversion ratio of diphenyl oxalate was 11.6%, the selectivity was 94.0%, and the yield was 10.9%.

Example 27

The decarbonylation reaction was repeated in the manner as described in Example 1, except that tetraphenylphosphonium chloride was replaced with 1.24 mmol of triphenylphosphine, 0.25 mmol of aluminum trichloride was added, and the reaction temperature was changed as set forth in Table 6.

It was confirmed that the conversion ratio of diphenyl oxalate was 91.7%, the selectivity was 93.0%, and the yield was 85.3%.

Examples 28 to 32

The decarbonylation reaction was repeated in the manner as described in Example 27, except that aluminum trichloride was replaced with the inorganic halogen atom-containing compound as set forth in Table 6, and the amount of diphenyl oxalate charged and the reaction temperature were changed as set forth in Table 6.

The reaction conditions and results are set forth in Table 6.

TABLE 6

| Example No. | Catalyst (5 mol. % to DPO) | Hal-Comp. (ratio) | DPO (mmol) | Tem. (°C.) | Time (hr.) | DPO Con. (%) | DPC Sel. (%) | DPC Yield (%) |
|---|---|---|---|---|---|---|---|---|
| Ex. 27 | Ph$_3$P | AlCl$_3$ (0.2) | 24.8 | 270 | 3 | 91.7 | 93.0 | 85.3 |
| Ex. 28 | Ph$_3$P | PtCl$_2$ (1) | 24.8 | 245 | 3 | 30.6 | 89.5 | 27.4 |
| Ex. 29 | Ph$_3$P | H$_2$PtCl$_6$ (1) | 24.8 | 245 | 3 | 52.6 | 93.1 | 49.0 |
| Ex. 30 | Ph$_3$P | RuCl$_3$ (0.8) | 24.8 | 245 | 3 | 27.8 | 80.1 | 22.3 |
| Ex. 31 | Ph$_3$P | SOCl$_2$ (1) | 20.7 | 255 | 3 | 96.6 | 88.1 | 85.1 |
| Ex. 32 | Ph$_3$P | Br$_2$ (1) | 20.7 | 255 | 3 | 97.2 | 95.6 | 92.9 |

Remarks: The amount of Hal-Comp. (i.e., halogen atom-containing compound) is indicated in terms of a molar ratio per one mole of the catalyst (i.e., organic phosphorous compound).

Examples 33 to 46

The decarbonylation reaction was repeated in the manner as described in Example 27, except that aluminum trichloride was replaced with the organic halogen atom-containing compound as set forth in Table 7, and the amount of diphenyl oxalate charged and the reaction temperature were changed as set forth in Table 7.

The reaction conditions and results are set forth in Table 7.

TABLE 7

| Example No. | Catalyst (5 mol. % to DPO) | Hal-Comp. (ratio) | DPO (mmol) | Tem. (°C.) | Time (hr.) | DPO Con. (%) | DPC Sel. (%) | DPC Yield (%) |
|---|---|---|---|---|---|---|---|---|
| Ex. 33 | Ph$_3$P | CHCl$_3$ | 20.7 | 255 | 3 | 32.4 | 86.1 | 27.9 |
| Ex. 34 | Ph$_3$P | CCl$_4$ | 20.7 | 255 | 3 | 98.5 | 95.8 | 94.4 |

TABLE 7-continued

| Example No. | Catalyst (5 mol. % to DPO) | Hal-Comp. (ratio) | DPO (mmol) | Tem. (°C.) | Time (hr.) | DPO Con. (%) | DPC Sel. (%) | DPC Yield (%) |
|---|---|---|---|---|---|---|---|---|
| Ex. 35 | Ph₃P | C₆H₅CH₂Cl | 20.7 | 255 | 3 | 97.3 | 84.5 | 82.2 |
| Ex. 36 | Ph₃P | (C₆H₅)₃CCl | 20.7 | 255 | 3 | 98.5 | 98.2 | 96.7 |
| Ex. 37 | Ph₃P | (C₆H₅)₂SiCl₂ | 20.7 | 255 | 3 | 98.5 | 84.6 | 83.3 |
| Ex. 38 | Ph₃P | ClCH₂CH₂CN | 20.7 | 255 | 3 | 91.3 | 83.6 | 76.3 |
| Ex. 39 | Ph₃P | ClCH₂COOH | 20.7 | 255 | 3 | 92.1 | 87.2 | 80.3 |
| Ex. 40 | Ph₃P | (COCl)₂ | 20.7 | 255 | 3 | 89.1 | 93.1 | 83.0 |
| Ex. 41 | Ph₃P* | CH₃(CH₂)₁₆COCl | 20.7 | 255 | 3 | 29.0 | 96.0 | 27.8 |
| Ex. 42 | Ph₃P | C₆H₅COCl | 20.7 | 255 | 3 | 92.8 | 85.8 | 79.6 |
| Ex. 43 | Ph₃P* | C₁₀H₇COCl | 20.7 | 260 | 3 | 47.0 | 98.0 | 46.1 |
| Ex. 44 | Ph₃P* | 2-thio-Cl | 20.7 | 260 | 3 | 35.0 | 99.0 | 34.7 |
| Ex. 45 | Ph₃P | p-tolu-Cl | 20.7 | 255 | 3 | 95.9 | 80.9 | 77.6 |
| Ex. 46 | Ph₃P | C₁₀H₇SO₂Cl | 20.7 | 255 | 3 | 74.6 | 79.0 | 58.9 |

Remarks:
*: 0.5 mol. %
The amount of Hal-Comp. (i.e., halogen atom-containing compound) employed is one mole to one mole of the catalyst, except the Examples 41 and 43 (3 moles per one mole of the catalyst) and Example 44 (2 moles per one mole of the catalyst).
(C₆H₅)₂SiCl₂: diphenyldichlorosilane
C₁₀H₇COCl: 2-naphthalenecarboxylic acid chloride
C₁₀H₇SO₂Cl: 2-naphthalenesulfonic acid chloride
2-thio-Cl: 2-thiophenecarboxylic acid chloride
p-tolu-Cl: p-toluenesulfonic acid chloride Example 47

The decarbonylation reaction was repeated in the manner as described in Example 1, except that tetraphenylphosphonium chloride was replaced with 1.24 mmol of triphenylphosphine oxide, 0.50 mmol of aluminum trichloride was added, and the reaction temperature was changed as set forth in Table 8.

It was confirmed that the conversion ratio of diphenyl oxalate was 53.5%, the selectivity was 94.0%, and the yield was 50.3%.

Examples 48 to 55

The decarbonylation reaction was repeated in the manner as described in Example 47, except that aluminum trichloride was replaced with the halogen atom-containing compound as set forth in Table 8, and the amount of diphenyl oxalate charged and the reaction temperature were changed as set forth in Table 8.

The reaction conditions and results are set forth in Table 8.

TABLE 8

| Example No. | Catalyst (5 mol. % to DPO) | Hal-Comp. | DPO (mmol) | Tem. (°C.) | Time (hr.) | DPO Con. (%) | DPC Sel. (%) | DPC Yield (%) |
|---|---|---|---|---|---|---|---|---|
| Ex. 47 | Ph₃P=O | AlCl₃ | 24.8 | 270 | 3 | 53.5 | 94.0 | 50.3 |
| Ex. 48 | Ph₃P=O | SOCl₂ | 20.7 | 255 | 3 | 88.2 | 86.5 | 76.3 |
| Ex. 49 | Ph₃P=O | CCl₄ | 20.7 | 255 | 3 | 37.0 | 99.3 | 36.7 |
| Ex. 50 | Ph₃P=O | C₆H₅CCl₃ | 20.7 | 255 | 3 | 98.4 | 81.9 | 80.6 |
| Ex. 51 | Ph₃P=O* | Br-xylene | 20.7 | 255 | 3 | 93.6 | 60.3 | 56.4 |
| Ex. 52 | Ph₃P=O | (COCl)₂ | 20.7 | 255 | 3 | 98.2 | 99.1 | 97.3 |
| Ex. 53 | Ph₃P=O | C₆H₅COCl | 20.7 | 255 | 3 | 97.9 | 85.8 | 84.0 |
| Ex. 54 | Ph₃P=O | p-tolu-Cl | 20.7 | 255 | 3 | 93.4 | 86.1 | 80.4 |
| Ex. 55 | Ph₃P=O | C₁₀H₇SO₂Cl | 20.7 | 255 | 3 | 67.4 | 76.6 | 51.6 |

Remarks:
*: 20 mol. %
The amount of Hal-Comp. (i.e., halogen atom-containing compound) employed is one mole to one mole of the catalyst, except the Example 47 (0.4 mole per one mole of the catalyst).
Br-xylene: α-bromo-o-xylene
p-tolu-Cl: p-toluenesulfonic acid chloride Example 56

The decarbonylation reaction was repeated in the manner as described in Example 1, except that the amount of tetraphenylphosphonium chloride was changed to 0.02 mmol, and the amount of diphenyl oxalate, the reaction temperature and the reaction time were changed as set forth in Table 9.

It was confirmed that the conversion ratio of diphenyl oxalate was 84.4%, the selectivity was 99.0%, and the yield was 83.6%.

Examples 57 to 59

The decarbonylation reaction was repeated in the manner as described in Example 56, except that a halogen atom-containing compound was added as set forth in Table 9.

The reaction conditions and results are set forth in Table 9.

Examples 60 to 67

The decarbonylation reaction was repeated in the manner as described in Example 1, except that tetraphenylphosphonium chloride was replaced with the tetraphenylphosphonium salt as set forth in Table 9, and the amount of diphenyl oxalate, the reaction temperature and the reaction time were changed as set forth in Table 9. In Examples 61 to 63 and 65 to 67, a halogen atom-containing compound was added as set forth in Table 9.

The reaction conditions and results are set forth in Table 9.

TABLE 9

| Example No. | Catalyst (mol. % to DPO) | Hal-Comp. (ratio) | DPO (mmol) | Tem. (°C.) | Time (hr.) | DPO Con. (%) | DPC Sel. (%) | DPC Yield (%) |
|---|---|---|---|---|---|---|---|---|
| Ex. 56 | $Ph_4P.Cl$ (0.1) | — | 20.7 | 280 | 2 | 84.4 | 99.0 | 83.6 |
| Ex. 57 | $Ph_4P.Cl$ (0.1) | $CHCl_3$ (5.5) | 20.8 | 280 | 2 | 94.0 | 99.0 | 93.1 |
| Ex. 58 | $Ph_4P.Cl$ (0.1) | $ClCOOC_6H_5$ (10) | 20.7 | 280 | 2 | 91.9 | 99.0 | 90.1 |
| Ex. 59 | $Ph_4P.Cl$ (0.1) | $PCl_5$ (8.1) | 20.7 | 280 | 2 | 95.4 | 99.0 | 94.4 |
| Ex. 60 | $Ph_4P.Br$ (0.5) | — | 20.7 | 260 | 1 | 13.0 | 77.0 | 10.0 |
| Ex. 61 | $Ph_4P.Br$ (0.5) | $CHCl_3$ (1.2) | 20.7 | 260 | 1 | 85.0 | 95.0 | 80.8 |
| Ex. 62 | $Ph_4P.Br$ (0.5) | $(COCl)_2$ (2.4) | 20.7 | 260 | 1 | 86.0 | 95.0 | 81.7 |
| Ex. 63 | $Ph_4P.Br$ (0.5) | HCl (300) | 20.7 | 260 | 1 | 80.9 | 96.0 | 77.7 |
| Ex. 64 | $Ph_4P.I$ (0.7) | — | 20.7 | 260 | 1 | 7.0 | 65.0 | 4.6 |
| Ex. 65 | $Ph_4P.I$ (0.7) | $(COCl)_2$ (1.1) | 20.7 | 260 | 1 | 84.0 | 84.0 | 70.6 |
| Ex. 66 | $Ph_4P.SCN$ (0.5) | $(COCl)_2$ (1.1) | 20.7 | 260 | 3 | 99.0 | 99.0 | 98.0 |
| Ex. 67 | $Ph_4P.CF_3CO_2$ (0.5) | $(COCl)_2$ (1.1) | 20.7 | 260 | 3 | 99.0 | 99.0 | 98.0 |

Remarks:
The amount of Hal-Comp. (i.e., halogen atom-containing compound) is indicated in terms of ratio per the amount of the catalyst.
$Ph_4P.SCN$: tetraphenylphosphonium thiocyanide
$Ph_4P.CF_3CO_2$: tetraphenylphosphonium trifluoroacetate Example 68

The decarbonylation reaction was repeated in the manner as described in Example 22, except that tetraphenylphosphonium chloride was replaced with phenoxytriphenylphosphonium chloride (5 mol. % to DPD). The phenoxytriphenylphosphonium chloride was prepared by the known process (Liebigs Ann. Chem., 1975, 406).

It was confirmed that the conversion ratio of diphenyl oxalate was 97.6%, the selectivity was 91.4%, and the yield was 89.2%.

Example 69

The decarbonylation reaction was repeated in the manner as described in Example 1, except that diphenyl oxalate was replaced with 1.30 g (4.18 mmol) of bis(4-chlorophenyl) oxalate, tetraphenylphosphonium chloride was employed in an amount of 5 mol. % based on the bis(4-chlorophenyl) oxalate, and the reaction time was changed to 20 minutes, to obtain 1.13 g (3.99 mmol) of bis(4-chlorophenyl) carbonate.

It was confirmed that the conversion ratio of bis(4-chlorophenyl) oxalate was 96.5%, the selectivity was 99.0%, and the yield was 95.5%.

What is claimed is:

1. A process for preparing a diaryl carbonate which comprises heating a diaryl oxalate in the presence of an organic phosphorous compound to release carbon monoxide therefrom.

2. The process for preparing a diaryl carbonate according to claim 1, wherein the organic phosphorous compound has a trivalent or pentavalent phosphorous atom.

3. The process for preparing a diaryl carbonate according to claim 1, wherein the organic phosphorous compound has at least one carbon-phosphorus bonding.

4. The process for preparing a diaryl carbonate according to claim 1, wherein the organic phosphorous compound is a phosphonium salt, a phosphine, a phosphine dihalide or a phosphine oxide.

5. The process for preparing a diaryl carbonate according to claim 1, wherein the organic phosphorous compound is a tetraarylphosphonium salt, a triarylphosphine, a triarylphosphine dihalide, or a triarylphosphine oxide.

6. The process for preparing a diaryl carbonate according to claim 1, wherein the organic phosphorous compound is a tetraarylphosphonium halide, a tetraarylphosphonium hydrogen dihalide, or a triarylphosphine dihalide.

7. A process for preparing a diaryl carbonate which comprises heating a diaryl oxalate in the presence of an organic phosphorous compound and a halogen atom-containing compound to release carbon monoxide therefrom.

8. The process for preparing a diaryl carbonate according to claim 7, wherein the organic phosphorous compound has a trivalent or pentavalent phosphorous atom.

9. The process for preparing a diaryl carbonate according to claim 7, wherein the organic phosphorous compound has at least one carbon-phosphorus bonding.

10. The process for preparing a diaryl carbonate according to claim 7, wherein the organic phosphorous compound is a phosphonium salt, a phosphine, a phosphine dihalide or a phosphine oxide.

11. The process for preparing a diaryl carbonate according to claim 7, wherein the organic phosphorous compound is a tetraarylphosphonium salt, a triarylphosphine, a triarylphosphine dihalide, or a triarylphosphine oxide.

12. The process for preparing a diaryl carbonate according to claim 7, wherein the organic phosphorous compound is a tetraarylphosphoniumhalide, a tetraarylphosphonium hydrogen dihalide, and a triarylphosphine dihalide.

13. The process for preparing a diaryl carbonate according to claim 7, wherein the halogen atom-containing compound is an organic or inorganic halide compound.

14. The process for preparing a diaryl carbonate according to claim 7, wherein the halogen atom-containing compound is at least one compound selected from the group consisting of halides of aluminum, halides of metals belonging to the platinum group, halides of phosphorus, hydrogen halides, halides of sulfur, and halogens.

15. The process for preparing a diaryl carbonate according to claim 7, wherein the halogen atom-containing compound is an organic compound having a C-Hal bonding, Hal meaning a halogen atom, a C-Si-Hal bonding, a —C(O)-Hal bonding, or a C—S(O)$_2$-Hal bonding.

16. The process for preparing a diaryl carbonate according to claim 7, wherein the halogen atom-containing compound is a chlorine atom-containing compound.

* * * * *